United States Patent
Handley et al.

(10) Patent No.: US 11,819,286 B2
(45) Date of Patent: Nov. 21, 2023

(54) APPARATUS FOR VISUALIZING A MOVABLE RADIATION SOURCE

(71) Applicants: MIRION TECHNOLOGIES (CANBERRA) INC., Meriden, CT (US); MIRION TECHNOLOGIES (CANBERRA) SAS, St Quentin en Yvelines (FR)

(72) Inventors: Joshua A. Handley, Meriden, CT (US); Michaël Ginsz, Lingolsheim (FR); Milan Zuvic, Lingolsheim (FR); Vlad Marian, Lingolsheim (FR); Peter Sandwall, Mansfield, OH (US)

(73) Assignees: MIRION TECHNOLOGIES (CANBERRA) SAS, St Quentin en Yvelines (FR); MIRION TECHNOLOGIES (CANBERRA) INC, Meriden, CT (US)

( * ) Notice: Subject to any disclaimer, the term of this patent is extended or adjusted under 35 U.S.C. 154(b) by 673 days.

(21) Appl. No.: 16/631,110

(22) PCT Filed: Jun. 25, 2018

(86) PCT No.: PCT/IB2018/000952
§ 371 (c)(1),
(2) Date: Jan. 14, 2020

(87) PCT Pub. No.: WO2020/002965
PCT Pub. Date: Jan. 2, 2020

(65) Prior Publication Data
US 2020/0222123 A1    Jul. 16, 2020

(51) Int. Cl.
*A61B 34/20* (2016.01)
*A61N 5/10* (2006.01)
(Continued)

(52) U.S. Cl.
CPC ............ *A61B 34/20* (2016.02); *A61N 5/1001* (2013.01); *G01T 1/2907* (2013.01);
(Continued)

(58) Field of Classification Search
CPC ............ A61B 34/20; A61B 2034/2057; A61B 2017/00725; A61N 5/1001;
(Continued)

(56) References Cited

U.S. PATENT DOCUMENTS 6,196,963 B1 * 3/2001 Williams ............. A61N 5/1007
600/3
9,880,329 B2 * 1/2018 Rossiger ............ G01N 23/2206
(Continued)

OTHER PUBLICATIONS

PCT International Search Report and Written Opinion from PCT/IB2018/000952 dated Mar. 18, 2019.
(Continued)

*Primary Examiner* — Keith M Raymond
*Assistant Examiner* — Sean A Frith
(74) *Attorney, Agent, or Firm* — Ladas & Parry, LLP

(57) ABSTRACT

An apparatus for visualizing a movable radiation source, the apparatus comprising: a radiation angular position sensor arranged for generating an angular position, with respect to a sensor axis, of a radiation source emitting radiations in front of said radiation angular position sensor; a camera having a camera axis distinct from the sensor axis; a light diverter arranged in front of said radiation angular position sensor for diverting toward the camera, light originally emitted in front of said radiation angular position sensor toward the radiation angular position sensor, the light diverter being arranged to not change the direction of radiations emitted in front of said radiation angular position sensor; and a composite image generator arranged for adding to a camera image captured by the camera a radiation source marker at a position derived from said angular
(Continued)

position and automatically scaled to the camera image size and resolution.

29 Claims, 8 Drawing Sheets

(51) Int. Cl.
  *G01T 1/29* (2006.01)
  *A61B 17/00* (2006.01)
  *A61M 25/01* (2006.01)
(52) U.S. Cl.
  CPC .............. *A61B 2017/00725* (2013.01); *A61B 2034/2057* (2016.02); *A61M 2025/0166* (2013.01); *A61N 2005/1054* (2013.01)
(58) Field of Classification Search
  CPC ......... A61N 2005/1054; G01T 1/2907; A61M 2025/0166
  See application file for complete search history.

(56) References Cited

U.S. PATENT DOCUMENTS

| | | | | |
|---|---|---|---|---|
| 10,617,401 | B2* | 4/2020 | Mihailescu | A61B 17/00234 |
| 2006/0108509 | A1* | 5/2006 | Frangioni | A61B 5/415 250/208.1 |
| 2009/0127459 | A1* | 5/2009 | Neustadter | G01T 1/2907 250/336.1 |
| 2009/0190722 | A1* | 7/2009 | Windt | A61B 6/06 378/206 |
| 2013/0168570 | A1* | 7/2013 | Wendler | A61B 6/583 250/336.1 |
| 2013/0195979 | A1* | 8/2013 | Tersigni | A61K 41/0052 424/490 |
| 2014/0303423 | A1* | 10/2014 | Amthor | A61N 5/1007 600/8 |
| 2015/0117613 | A1* | 4/2015 | Satoh | G01T 7/00 378/98.12 |
| 2016/0187269 | A1* | 6/2016 | Brady | G01N 23/207 378/87 |
| 2017/0304652 | A1* | 10/2017 | Belley | A61N 5/1075 |
| 2019/0200848 | A1* | 7/2019 | McDowall | G06V 20/20 |

OTHER PUBLICATIONS

PCT International Preliminary Report on Patentability (Chapter I) with Written Opinion from PCT/IB2018/000952 dated Dec. 29, 2020.

\* cited by examiner ately to a proximity of the region of the body that must be

APPARATUS FOR VISUALIZING A MOVABLE RADIATION SOURCE

CROSS-REFERENCE TO RELATED APPLICATION

The present application is the U.S. national phase application of PCT Application No. PCT/IB2018/000952 filed on Jun. 25, 2018, the disclosure of which is incorporated herein in its entirety by reference.

TECHNICAL FIELD

This presentation is directed in general to the field of radiation detectors and in particular to an apparatus for visualizing a movable radiation source, such as a radiation source for brachytherapy.

BACKGROUND

Brachytherapy is a form of radiotherapy where a short range radiation source is placed inside or next to an area of the body that requires treatment. The radiation-source can be enclosed in a capsule that can be implanted surgically, generally to be removed at the end of the treatment. Alternatively, the radiation source can be attached at the end of a wire or endoscope, thus allowing to introduce for a controlled time the source in a patient's body via a natural or surgical orifice, before recovering the source by retrieving the wire or endoscope. The source can be a high activity (~10 Curie) Ir192 source, and can have approximately the size of a grain of rice.

A source attached to the end of a wire is generally held in a shielded enclosure when not in use, so as to not unduly expose caregivers or patients to radiations. A dispensing tube or catheter can have a proximal end coupled to the shielded enclosure, where the distal end of the dispensing tube is provided for being introduced in the patient up to a close proximity of a region of the body that must be irradiated. The wire holding the source can be wound on a remotely controlled spindle, arranged such that winding or unwinding the spindle moves the radiation source into or out of the shielded enclosure, inside a lumen of the dispensing tube.

A patient who is to be treated is installed in a shielded room close to the shielded enclosure, and the distal end of the dispensing tube is arranged in proximity of the region of the patient's body that must be irradiated; for example through a natural orifice of the body. The caregiver then leaves the shielded room and remotely unwinds the spindle so as to move the source outside of the shielded enclosure, and inside the dispensing tube until the source reaches a proximity of the region of the body that must be irradiated. Because the caregiver is not present in the shielded room when the source is moved outside of the shielded enclosure, it is very important to know precisely by how much the spindle must be unwound to bring the source to near the end of the tube. Due to human or material error however, the spindle can be unwound too little, which causes the source to not irradiate the proper portion of the patient's body. Also due to human or material error, the spindle can be unwound too much, thus pushing the source too far into the patient's body and potentially not irradiating a proper portion of the body or puncturing an organ, or increasing the odds of breaking the tip of the wire and losing the source in the patient's body. The wire holding the source can also break due to mechanical failure while unwinding or winding the spindle, thus leaving the source stranded in a section of the dispensing tube, and making the dispensing tube a permanent source of unshielded radiations.

Currently, the caregivers have no practical means for visualizing the location of the mobile radiation source. The caregivers can only use radiation area monitors that indicate that the source is not present inside the shielded enclosure. As outlined above, a radiation source such as a brachytherapy source can also come under the form of a small implantable source. If for whatever reason a source is lost (e.g. dropped or misplaced) during a procedure, it is very important to locate and retrieve such lost source as rapidly as possible. Presently, such sources can only be detected globally, for example using a Geiger counter, then located visually.

FIG. 1A illustrates a known system 10 such as the Mirion product known under the commercial name "iPIX", which comprises a coded mask aperture radiation sensor 12 and an optical camera 14, and superpose a radioactivity mapping generated by the radiation sensor onto a visible light image captured by the camera. A radiation source 16 is illustrated in the field of view, respectively 12' and 14' of each of the radiation sensor 12 and the camera 14. As illustrated in FIG. 1B, the radiation sensor 12 generates a radioactivity mapping 18 showing the position 16' of source 16 in its field of view 12'. As illustrated in FIG. 1C, the camera 14 generates an image 20 showing inter alia a picture 16" of source 16 in its field of view 14'. It appears immediately that due to parallax, the respective positions 16' and 16" in mapping 18 and image 20 are different. Accordingly, system 10 comprises correction means 11 that generate a corrected position 16'" of source 16 in picture 20 based on position 16' in mapping 18.

A problem with system 10 is that the parallax between mapping 18 and image 20 depends on the distance between for example sensor 12 and source 16. However, system 10 comprises no means to measure the distance between the sensor 12 and the source 16, which could allow to automatically correct the parallax.

Correction means 11 receive from sensor 12 and camera 14 uncorrected mapping 18 and image 20, and comprises a manual calibration input 15 that allows memorizing how to generate an image 20 with a corrected source position 16'" upon having a user align the position 16' in radioactivity mapping 18 with the position 16" in picture 20 of source 16. To ease the user calibration, a source 16 having an easily recognizable image in picture 20 can be used.

A drawback however of such a manual calibration is that it must be conducted each time the distance between the source 16 and the system 10 changes. Thus, if system 10 allows visualizing reliably and accurately the position of an immobile radiation source, system 10 becomes inaccurate when the radiation source is a movable source. Inaccurately visualizing the position of a radiation source can be very detrimental for example when the caregiver wants to know if the source is appropriately positioned with respect to the patient. Means to measure the distance between the sensor 12 and a source exist, such as laser pointers or time-of-flight cameras. However, such means only give satisfactory results for large, immobile sources. Attempts at providing means to measure the distance between the sensor 12 and the source 16 have so far been unsuccessful for small mobile sources.

Accordingly, there exists a need for a device that would accurately visualize in real time the position of a movable radiation source such as a brachytherapy source.

SUMMARY

To address one or more of the above-deficiencies of the prior art, an embodiment described in this presentation relates to an apparatus for visualizing a movable radiation source, the apparatus comprising: a radiation sensor having a sensor axis; a camera having a camera axis distinct from the sensor axis; a light diverter arranged in front of the radiation sensor for diverting toward the camera light originally emitted toward the radiation sensor, the light diverter being arranged to not change the direction of radiations emitted toward said radiation sensor; and a composite image generator arranged for adding to a camera image captured by the camera a radiation source marker having a corrected position derived from an output of the radiation sensor and automatically scaled to the camera image size and resolution.

An embodiment of this presentation comprises an apparatus for visualizing a movable radiation source, the apparatus having: a radiation angular position sensor arranged for generating an angular position, with respect to a sensor axis, of a radiation source emitting radiations in front of said radiation angular position sensor; a camera having a camera axis distinct from the sensor axis; a light diverter arranged in front of said radiation angular position sensor for diverting toward the camera, light originally emitted in front of said radiation angular position sensor toward the radiation angular position sensor, the light diverter being arranged to not change the direction of radiations emitted in front of said radiation angular position sensor; and a composite image generator arranged for adding to a camera image captured by the camera a radiation source marker at a position derived from said angular position and automatically scaled to the camera image size and resolution.

According to an embodiment of said presentation, said radiation angular position sensor comprises a pixelated radiation sensor having said radiation sensor axis, a radiation mask with a coded aperture being arranged in a plane normal to said radiation sensor axis in front of said pixelated radiation sensor.

According to an embodiment of said presentation, said light diverter comprises a mirror arranged for reflecting light and letting radiations pass through.

According to an embodiment of said presentation, the composite image generator is arranged to be calibrated by, in an initial state, moving a radiation source to at least two source positions in the field of view of the radiation sensor, recording at least two angular positions provided by the sensor at said at least two source positions and recording at least two corresponding camera positions of a picture of said radiation source in a camera image captured by the camera; calculating a sensor distance between said at least two source positions based on said at least two angular positions; calculating a camera distance between said at least two corresponding camera positions; and calculating a ratio of said sensor distance and said camera distance; the composite image generator being arranged to use said ratio for automatically scaling said position derived from said angular position to the camera image size and resolution.

According to an embodiment of said presentation, said composite image generator comprises a user interface arranged for allowing a user to point to positions of a picture of the radiation source in said camera image, the composite image generator being arranged for storing said positions as well as corresponding angular positions generated by the sensor.

According to an embodiment of said presentation, said light is comprised in the wavelength range of 300 nm to 1 mm.

According to an embodiment of said presentation, said light is comprised in the wavelength range of 380 nm to 750 nm.

According to an embodiment of said presentation, said radiations are comprised in the wavelength range of 0.01 to 10 nanometers.

According to an embodiment of said presentation, said radiations are comprised in the wavelength range of 0.01 to 1 nanometers. According to an embodiment of said presentation, said radiations have energies comprised in the range of 100 eV to 1 MeV.

According to an embodiment of said presentation, said radiation angular position sensor arranged for generating said angular position for a radiation source having an intensity comprised between 1 microCuries and 100 Curies, located in a range of 0.5 to 100 meters from said sensor.

According to an embodiment of said presentation, said radiation sensor, said camera and said composite image generator are arranged to generate a new composite image with a period comprised between 1 millisecond and 1 hour.

Another embodiment of said presentation, comprises an apparatus for visualizing a movable radiation source, the apparatus having: a radiation angular position sensor including a pixelated radiation sensor having said radiation sensor axis, a radiation mask with a coded aperture being arranged in a plane normal to said radiation sensor axis in front of said pixelated radiation sensor; where said radiation mask comprises no aperture along said radiation sensor axis; the radiation angular position sensor being arranged for generating an angular position, with respect to said radiation sensor axis, of a radiation source emitting radiations in front of said radiation angular position sensor; a camera having a camera axis identical to the sensor axis; the camera being arranged in front of said radiation mask and being sized so as to not overlap an aperture of the mask; and a composite image generator arranged for adding to a camera image captured by the camera a radiation source marker at a position derived from said angular position and automatically scaled to the camera image size and resolution.

According to an embodiment of said presentation, the composite image generator is arranged to be calibrated by, in an initial state, moving a radiation source to at least two source positions in the field of view of the radiation sensor, recording at least two angular positions provided by the sensor at said at least two source positions and recording at least two corresponding camera positions of a picture of said radiation source in a camera image captured by the camera; calculating a sensor distance between said at least two source positions based on said at least two angular positions; calculating a camera distance between said at least two corresponding camera positions; and calculating a ratio of said sensor distance and said camera distance; the composite image generator being arranged to use said ratio for automatically scaling said position derived from said angular position to the camera image size and resolution.

According to an embodiment of said presentation, said composite image generator comprises a user interface arranged for allowing a user to point to positions of a picture of the radiation source in said camera image, the composite image generator being arranged for storing said positions as well as corresponding angular positions generated by the sensor.

According to an embodiment of said presentation, said light is comprised in the wavelength range of 300 nm to 1 mm.

According to an embodiment of said presentation, said light is comprised in the wavelength range of 380 nm to 750 nm.

According to an embodiment of said presentation, said radiations are comprised in the wavelength range of 0.01 to 10 nanometers.

According to an embodiment of said presentation, said radiations are comprised in the wavelength range of 0.01 to 1 nanometers.

According to an embodiment of said presentation, said radiations have energies comprised in the range of 100 eV to 1 MeV.

According to an embodiment of said presentation, said radiation angular position sensor arranged for generating said angular position for a radiation source having an intensity comprised between 1 microCuries and 12 Curies, located in a range of 0.5 to 100 meters from said sensor.

According to an embodiment of said presentation, said radiation sensor, said camera and said composite image generator are arranged to generate a new composite image with a period comprised between 1 millisecond and 1 hour.

Another embodiment of said presentation comprises a brachytherapy system having: a catheter having a lumen between a distal end and a proximal end; a radiation source capable of passing through said lumen; a shield enclosure arranged for receiving the radiation source, the proximal end of the catheter being coupled to the shield enclosure; a radiation source actuator arranged for moving the radiation source out of the shield enclosure into said lumen toward the distal end of the catheter; and any one of the apparatuses for visualizing a movable radiation source as herein disclosed, arranged for visualizing said radiation source in said catheter.

According to an embodiment of said presentation, the brachytherapy system comprises a processor arranged to issue an alarm signal if the radiation source is outside the shield enclosure and does not move despite the radiation source actuator being actuated.

According to an embodiment of said presentation, the brachytherapy system comprises a processor arranged to determine the outline of a patient in the image acquired by the camera, and arranged to issue an alarm signal if the radiation source remains more than a predetermined time outside the shield enclosure and outside of said outlines of a patient.

According to an embodiment of said presentation, the camera is arranged for detecting infrared light.

Although specific advantages have been enumerated above, various embodiments may include some, none, or all of the enumerated advantages. Additionally, other technical advantages may become readily apparent to one of ordinary skill in the art after review of the following figures and description.

BRIEF DESCRIPTION OF THE DRAWINGS

For a more complete understanding of this presentation and its advantages, reference is now made to the following description taken in conjunction with the accompanying drawings, in which like reference numerals represent like parts.

DETAILED DESCRIPTION

It should be understood at the onset that, although example embodiments are illustrated below, the present technology may be implemented using any number of techniques, whether currently known or not. The present technology should in no way be limited to the example implementations, drawings, and techniques illustrated below. Additionally, the drawings are not necessarily drawn to scale.

Figure 1A:
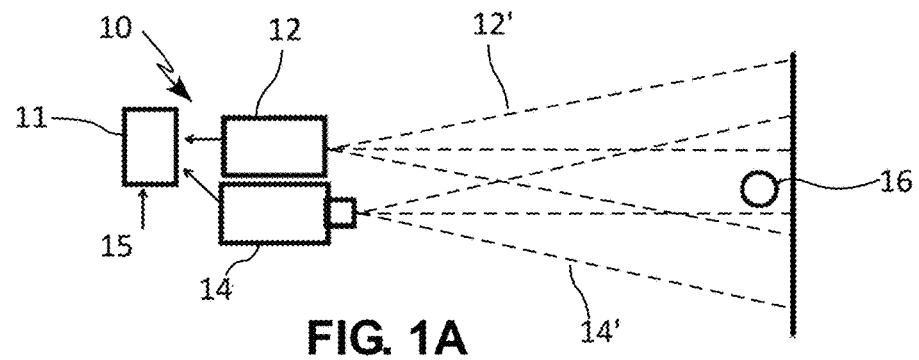
FIG. 1A illustrates a known apparatus for visualizing immobile radiation sources.
Figure 2A:
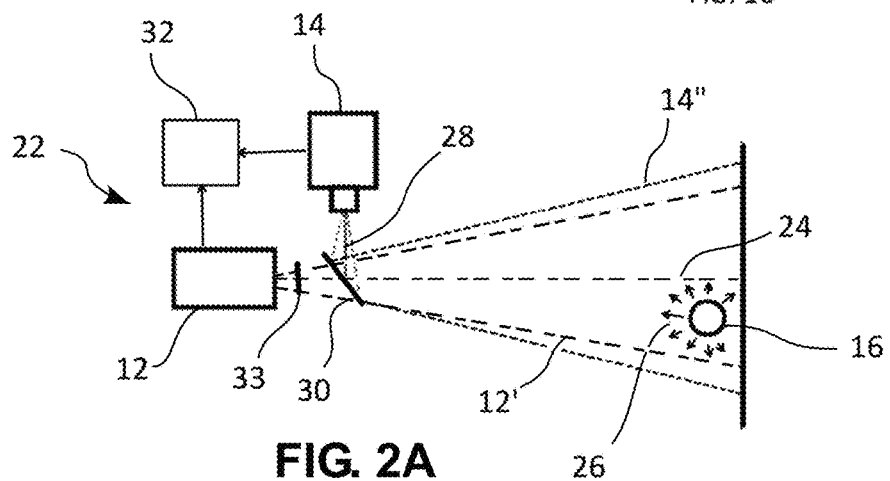
FIG. 2A illustrates an embodiment of an apparatus according to this presentation for visualizing a movable radiation source.

FIG. 2A illustrates an apparatus 22 for visualizing a movable radiation source 16 according to an embodiment of this presentation; the apparatus comprising a radiation angular position sensor 12 that can be the same as the sensor illustrated in FIG. 1A. As detailed thereafter, sensor 12 can generate an angular position, with respect to a sensor axis 24, of an observed radiation source 16 as said source emits radiations 26 in the field of view of sensor 12. According to an embodiment of this presentation, apparatus 22 further comprises a camera 14 having a camera axis 28 distinct from the sensor axis 24. The camera 14 can be of the same type as the camera 14 illustrated in FIG. 1A.

Figure 1B:
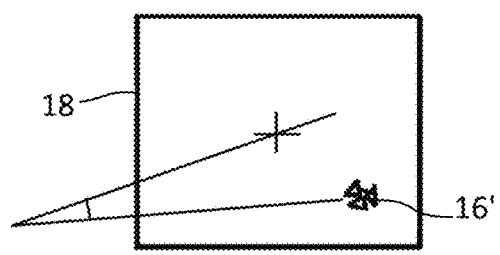
FIGS. 1B and 1C illustrate the operation of the apparatus of FIG. 1A.
Figure 1C:
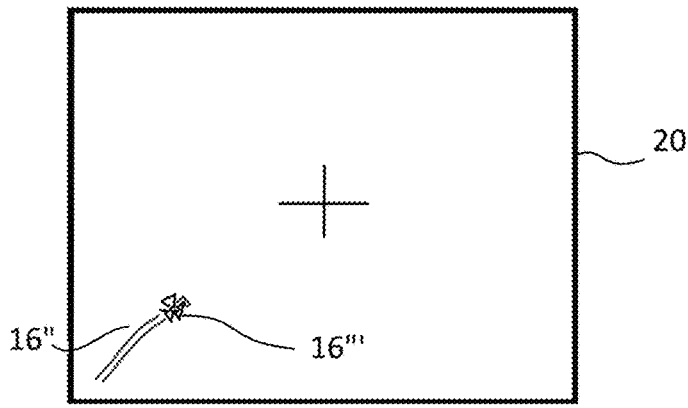

According to an embodiment of this presentation, apparatus 22 further comprises a light diverter 30 arranged in front of sensor 12 for diverting toward camera 14 the light directed at sensor 12, and arranged to not change the direction of radiations directed at radiation angular position sensor. An effect of light diverter 30 is that the field of view 12' of the sensor 12 can be the same as in FIG. 1, while the field of view 14" of camera 14 away from apparatus 22 can be centered on the axis 24 of the field of view 12' of sensor 12.

Even though light diverter 30 is illustrated in FIG. 2A as comprising a single mirror arranged for reflecting light and letting radiations pass through, angled at 45 degrees with respect to perpendicular axis 24 and 28, other embodiments of light diverter 30 can comprise a plurality of mirrors (for example two reciprocating mirrors if axis 24 and 28 were parallel), or can use different angles if axis 24 and 28 are not perpendicular.

According to an embodiment of this presentation, camera 14 is provided for detecting light comprised in the wavelength range of 300 nm to 1 mm; preferably in the wavelength range of 380 nm to 750 nm. According to an embodiment of this presentation, sensor 12 is provided for detecting radiations comprised in the wavelength range of 0.01 to 10 nanometers; preferably in the wavelength range of 0.01 to 1 nanometers. According to an embodiment of this presentation, sensor 12 is provided for detecting radiations comprised in the range of 100 eV to 1 MeV. Camera 14 can be an industrial-grade full HD (1080p) visible camera operating in USB 3.0.

Figure 2B:
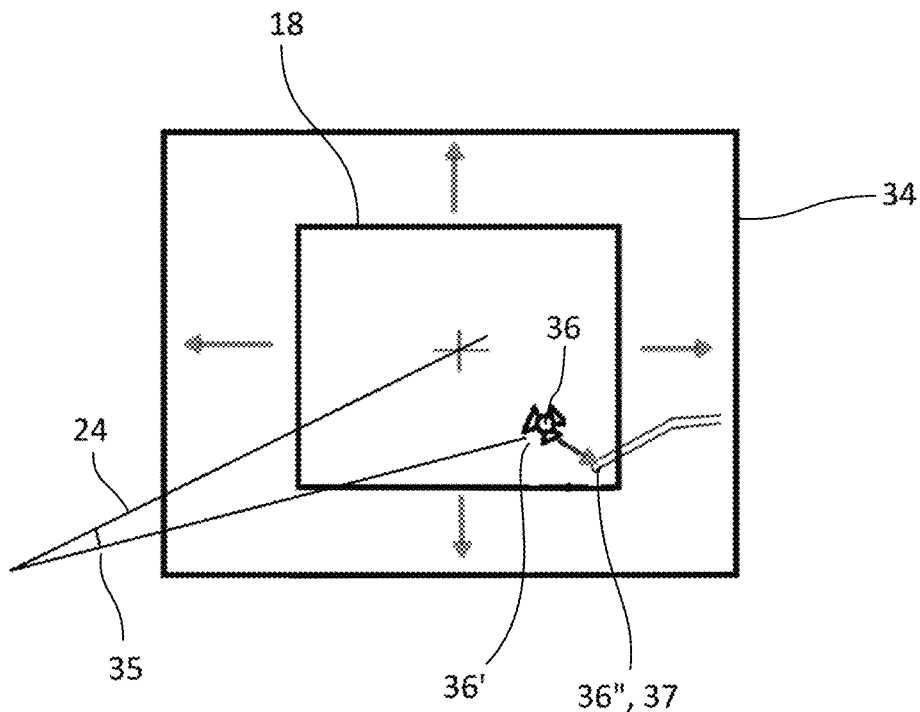
FIGS. 2B and 2C illustrate the operation of the apparatus of FIG. 2A.

According to an embodiment of this presentation, apparatus 22 further comprises a composite image generator 32 arranged for, as illustrated in FIG. 2B, adding to a camera image 34 captured by the camera 14 a radiation source marker 36 at a corrected position 36". Corrected position 36" is generated based on the output of sensor 12. In the embodiment where sensor 12 is a coded mask aperture radiation sensor, sensor 12 outputs an angular position 35 of a detected source with respect to the axis 24 of the field of view of sensor 12. Sensor 12 then generates a mapping 18 having a source position 36', wherein mapping 18 pictures a fictitious plane normal to the sensor axis that comprises the observed source, wherein the edges of mapping 18 represent the intersection of the field of view of sensor 12 and said fictitious plane.

Position 36' can for example be expressed as X and Y coordinates in a referential that depends on the number of pixels in sensor 12; i.e. that depends on the resolution of sensor 12. It is to be noted that, due to light diverter 30, the centers of image 34 and mapping 18 are made identical. However, due to structural differences between the optics and resolution of sensor 12 and camera 14, a same distance in image 34 and mapping 18 may represent different actual distances. Consistently, a same actual distance can appear as two different distances in image 34 and mapping 18. It follows that the position 36' may have to be scaled to the camera image size and resolution by a multiplying factor, for example equal to a size ratio of a same actual distance as measured in mapping 18 and image 34. A single multiplying factor can be used on the X and Y coordinates of position 36' in case the scale difference between camera 14 and sensor 12 is identical in the X and Y directions. In case the scale difference between camera 14 and sensor 12 is different in the X and Y directions, a different size ratio can be calculated (and applied for scaling) for each of the X and Y directions.

According to an embodiment of this presentation, composite image generator 32 can comprise optical elements such as lenses 33 that make the field of views of camera 14 and sensor 12 more alike. According to an embodiment of this presentation, composite image generator 32 can comprise optical elements such as lenses that make the field of views of camera 14 and sensor 12 completely alike, and the resolutions of the sensor and camera can be identical or nearly identical, in which case the scaling of the position 36' into position 36" can be conducted exclusively by the lenses of composite image generator 32.

FIG. 2B shows position 36' as it appears on mapping 18, and corrected position 36" as it appears on image 34. FIG. 2B also illustrates a picture 37 of the source as it appears on image 34 (here a rice-grain sized source at the end of a wire).

Figure 2C:
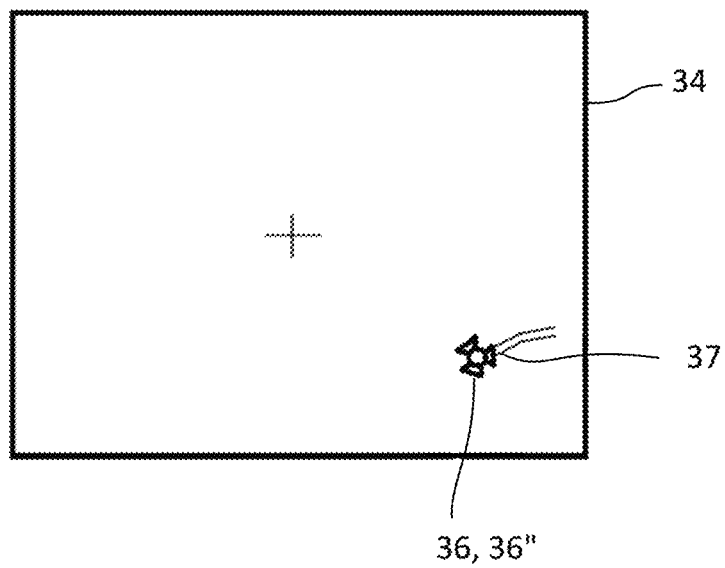

FIG. 2C illustrates the final image 34 as output by composite image generator 32, comprising a picture 37 of the radiation source as well as a radiation source marker 36 displayed at position 36", i.e. on top of picture 37. According to an embodiment of this presentation, marker 36 can have a degree of transparency. According to an embodiment of this presentation, marker 36 can have a predetermined color.

According to an embodiment of this presentation, the scaling of the position 36' into corrected position 36" is automatically conducted by composite image generator 32.

Importantly, composite image generator 32 needs only be calibrated once, and does not need to be re-calibrated even if the observed source is moving.

Figure 3A:
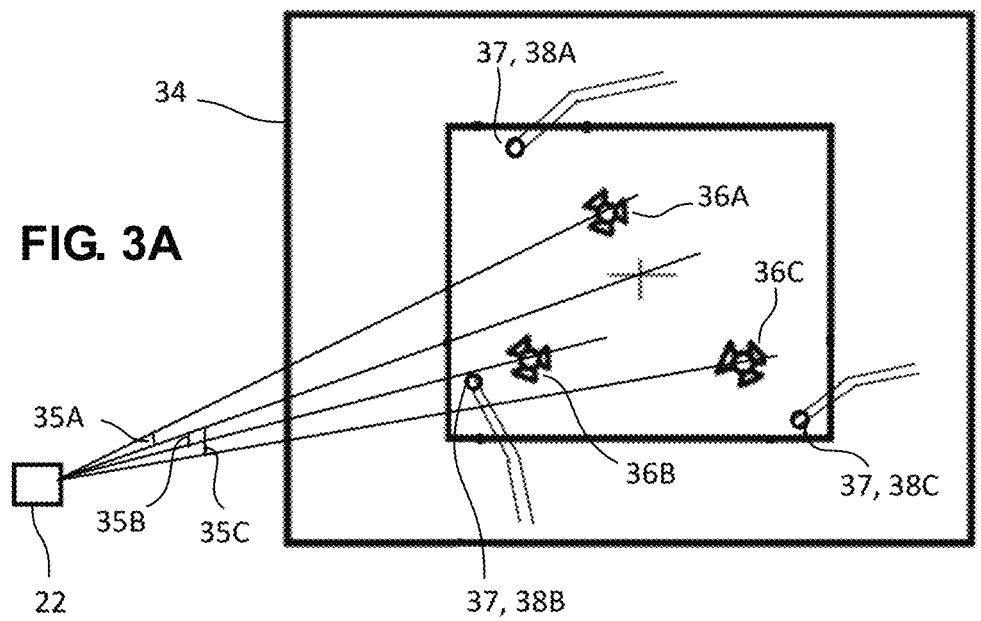
FIG. 3A illustrates a calibration process of an apparatus according to an embodiment of this presentation.

FIG. 3A illustrates a calibration process of the composite image generator that comprises successively placing in the field of view of the radiation sensor 12 a radiation source 35 in at least two source positions, recording the angular positions (35A, 35B, 35C) that correspond to each source position and recording the at least two corresponding camera positions (38A, 38B, 38C) of the picture 37 of said radiation source in camera image 34. According to an embodiment of this presentation, the calibration further comprises calculating a sensor distance between at least two source positions (36A, 36B, 36C) in mapping 18, themselves based on the recorded angular positions (35A, 35B, 35C) for example as detailed above; calculating a camera distance based on said at least two corresponding camera positions in image 34; and calculating a ratio of said sensor distance and said camera distance; the composite image generator being arranged to use said ratio for automatically scaling said position derived from said angular position to the camera image size and resolution.

Figure 3B:
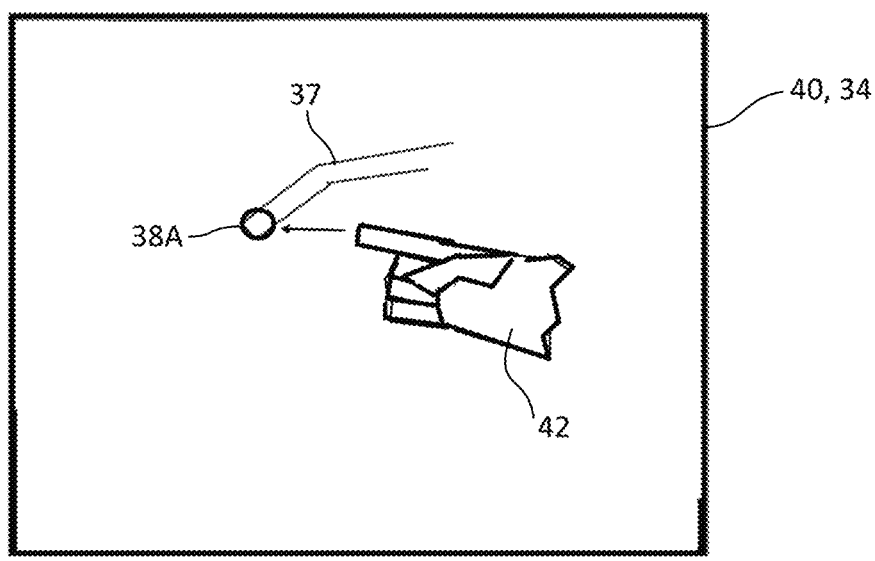
FIG. 3B illustrates a graphical user interface of an apparatus according to an embodiment of this presentation.
Figure 3B:

As illustrated in FIG. 3B, according to an embodiment of this presentation, composite image generator 32 can comprise a user interface (for example a mouse (not shown), or a touch-screen graphical user interface integrated to a display 40 that displays image 34, arranged for allowing a user 42 to point to the positions (38A, 38B, 38C) of the picture 37 of the radiation source in image 34, and for prompting (44) a memory (not shown) to store said positions (38A, 38B, 38C) as well as their corresponding angular positions (35A, 35B, 35C) generated by the sensor 12.

According to an embodiment of this presentation, camera 14 and composite image generator 32 are arranged to generate a new composite image with a period comprised between 1 and 100 milliseconds.

Figure 4:
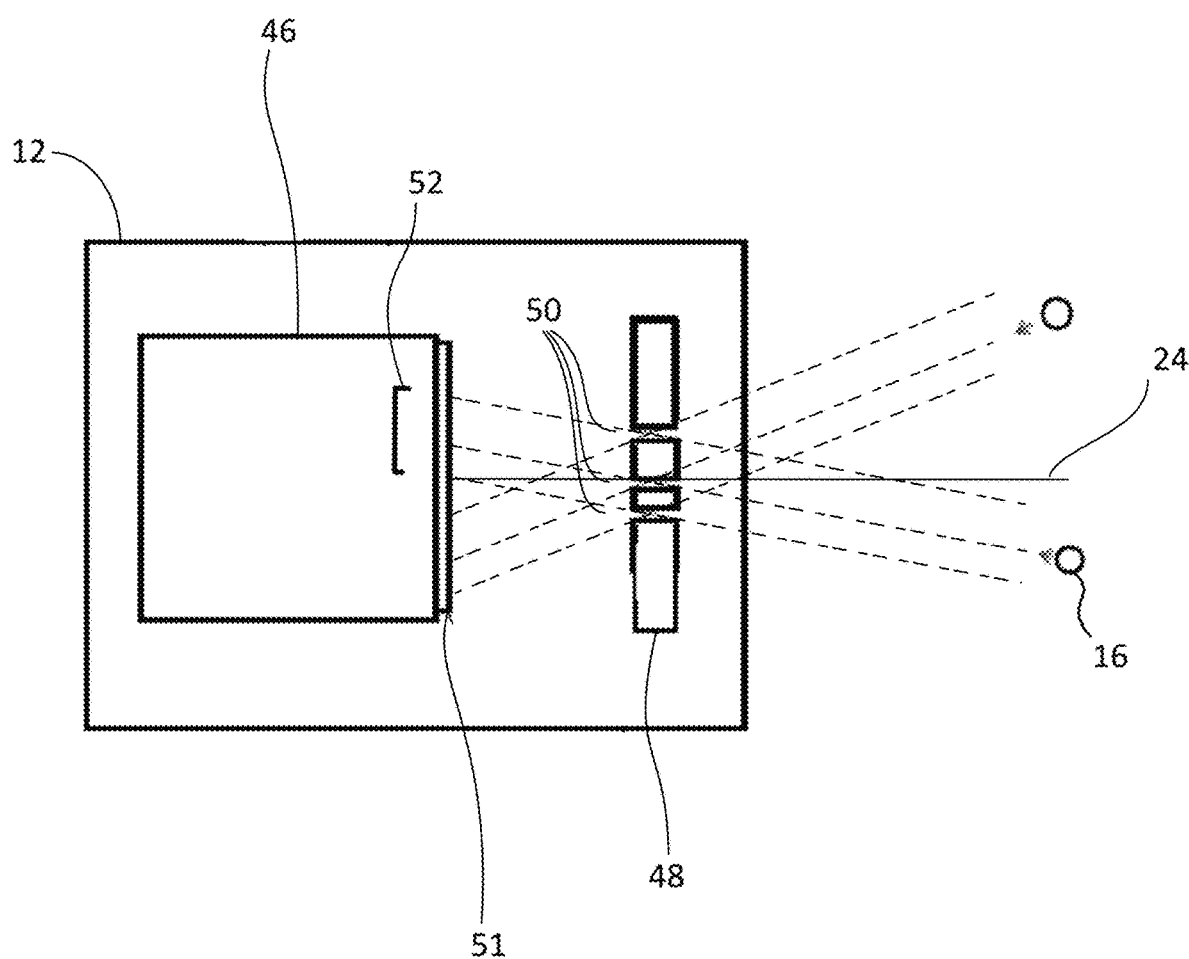
FIG. 4 illustrates a radiation angular position sensor according to an embodiment of this presentation.

FIG. 4 illustrates a radiation angular position sensor 12 according to an embodiment of this presentation, comprising a pixelated radiation sensor 46 having a sensor axis 24, and a radiation mask 48 with a coded aperture 50 arranged in a plane normal to axis 24 in front of pixelated radiation sensor 46. Essentially, sensor 46 is arranged for detecting a position on a sensing area 51 of an image 52 of the coded aperture 50 illuminated by a radiation source 16, and for calculating the angular position of source 16 based on the position of image 52 with respect to axis 24.

According to an embodiment of this presentation, radiation angular position sensor 12 is arranged for generating an angular position for a radiation source having an intensity comprised for between 1 and 12 Curies, located in a range of 0.5 to 10 meters from the sensor, for a fast detection of a small source such as for brachytherapy. It is to be noted that smaller/weaker sources (of the order of one microCurries to several microCuries) can be located using an apparatus according to this presentation, if the acquisition time of the sensor is made larger (such as taking a plurality of minutes of acquisition per frame). Similarly, stronger sources than noted above (such as up to 100 Curies) can be detected at longer distances (such as up to 100 meter).

According to an embodiment of this presentation, sensor 12 can comprise a pixelated CdTe-based sensor 46 (256×256 pixels of 55$m$ pitch) having a pixel readout system in communication with a PC via USB 3.0 and a high voltage power supply to polarize the detector are also included in the gamma camera module. Coded aperture mask 48 can be a 4 mm thick tungsten collimator having patterned 50 holes, placed about 15 mm in front of gamma sensor 46 to project an image 52 of the gamma source onto the sensor.

It is to be noted that, if a CdTe sensor can be used, other sensors can also be used, such as sensors based on CZT, Silicon, Germanium or Gallium Arsenide. It is noted that, if the sensor can have 256×256 pixels with a 55 µm pitch, any other pixel pitch, number and arrangement could potentially give similar results. It is noted that coded aperture masks different from the one exemplified hereabove can also be used, as long as their thickness, hole size, number or pattern could are appropriate.

Figure 5A:
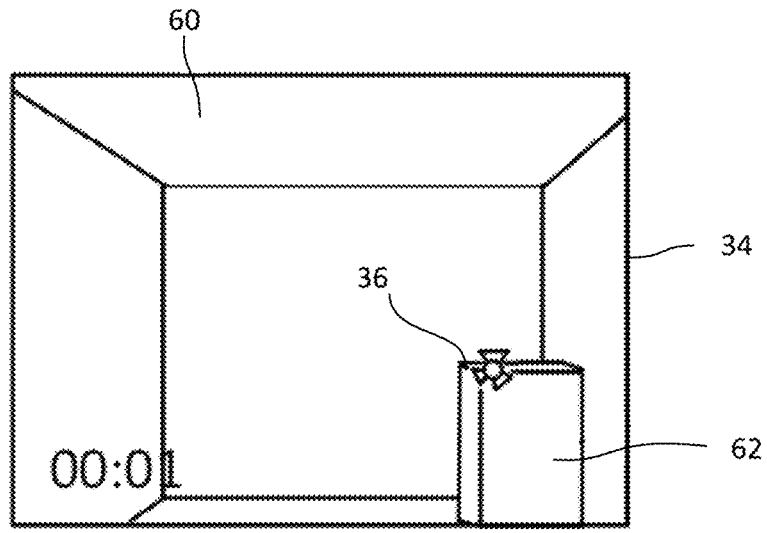
FIGS. 5A to 5C illustrate the operation of an apparatus according to an embodiment of this presentation.
Figure 5B:
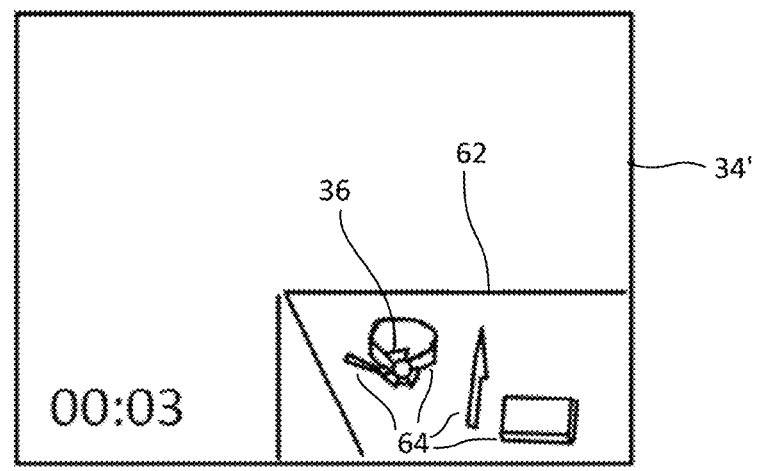
Figure 5C:
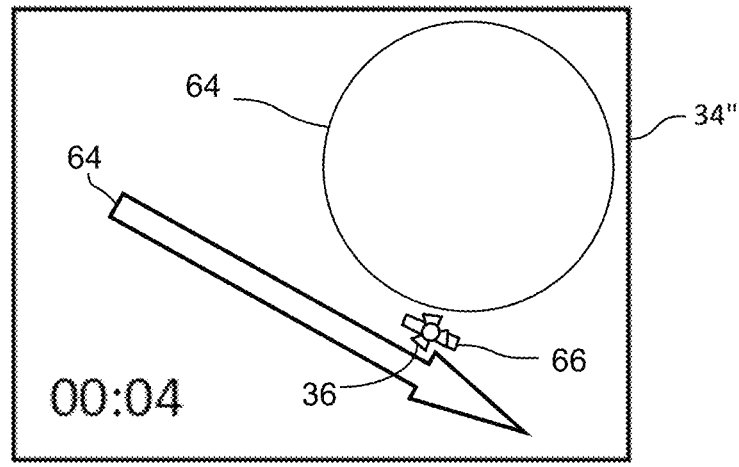

FIGS. 5A to 5C illustrate the finding of a lost source of radiation in a room by the operation of an apparatus 22 (not shown) according to an embodiment of this presentation. FIG. 5A illustrates an image 34 produced by apparatus 22 (by composite image generator 32), as visible in real time by a user, showing the walls of a room 60 furnished with a piece of furniture 62; as well as a radioactive source marker 36.

FIG. 5B illustrates a close-up image 34' as obtained when the user moves apparatus 22 closer to the location of radiation source marker 36 in the room, on top of the piece of furniture 62 where a number of objects 64 can be distinguished.

FIG. 5C illustrates a further close-up image 34" as obtained when the user moves apparatus 22 even closer to the location of radiation source marker 36, to a position where it appears visually that source marker 36 overlays the picture 66 of a rice-grain-sized radiation source that was for example forgotten on top of furniture 62 after a surgical procedure. As illustrated in FIGS. 5A, 5B and 5C, an apparatus according to this presentation allows moving rapidly toward a detected source of radiation, and thus for example allows limiting greatly accidental exposure to radiations. According to an embodiment of this presentation, apparatus 22 can be provided for visualizing the position of radiation sources having an energy of from 10 or 20 keV to 1 MeV.

Figure 6:
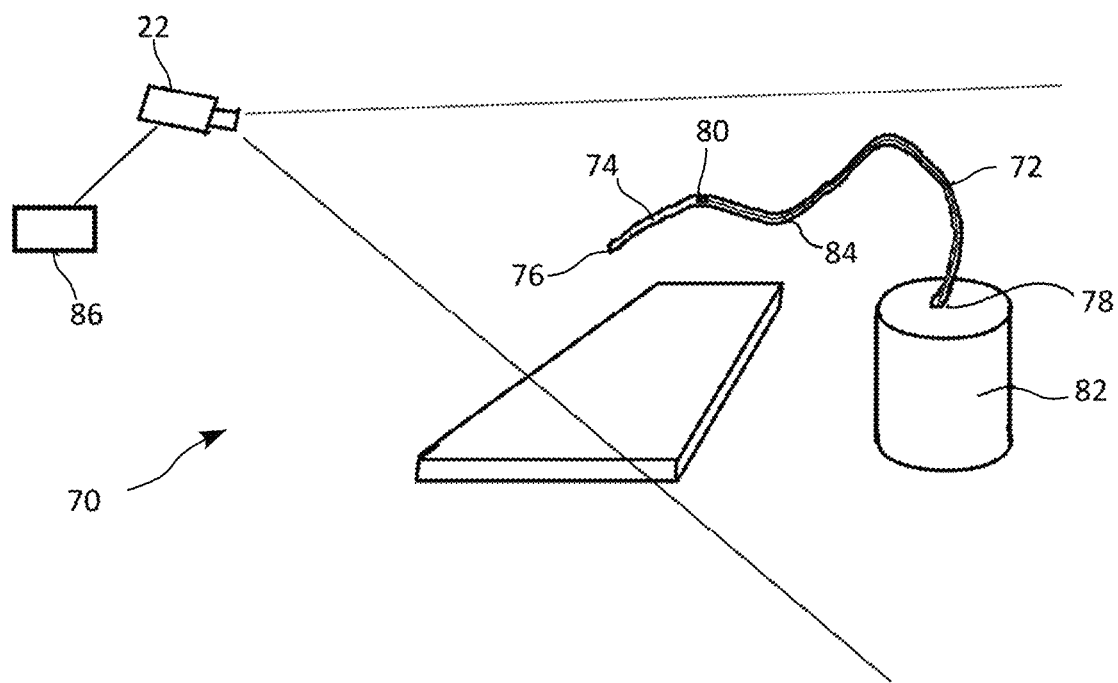
FIG. 6 illustrates a brachytherapy system according to an embodiment of this presentation.

FIG. 6 illustrates a brachytherapy system 70 according to an embodiment of this presentation, comprising a catheter 72 having a lumen 74 between a distal end 76 and a proximal end 78; a radiation source 80 capable of passing through lumen 74; a shield enclosure 82 arranged for receiving the radiation source 80, the proximal end 78 of the catheter 72 being coupled to the shield enclosure 82; and a radiation source actuator 84 (for example a metal wire having a distal end coupled to source 80 and a proximal end wound on a controllable electric spindle—not shown—) arranged for moving the radiation source 80 out of the shield enclosure 82 into lumen 74 toward the distal end 76 of the catheter 72, and back. According to embodiments of this presentation, system 70 further comprises an apparatus 22 for visualizing a movable radiation source as detailed above, arranged for visualizing radiation source 80 in catheter 72.

According to an embodiment of this presentation, system 70 can comprise a processor 86 arranged to issue an alarm signal if the radiation source 80 is outside the shield enclosure 82 and does not move despite the radiation source actuator 84 being actuated.

Figure 7A:
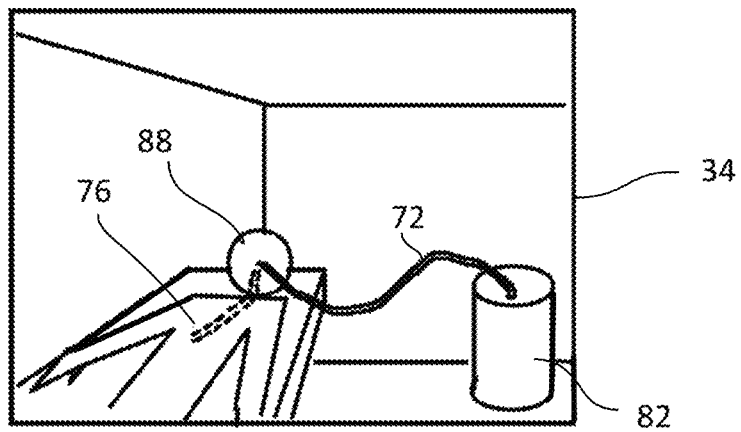
FIGS. 7A to 7C illustrate the operation of a system according to an embodiment of this presentation.
Figure 7B:
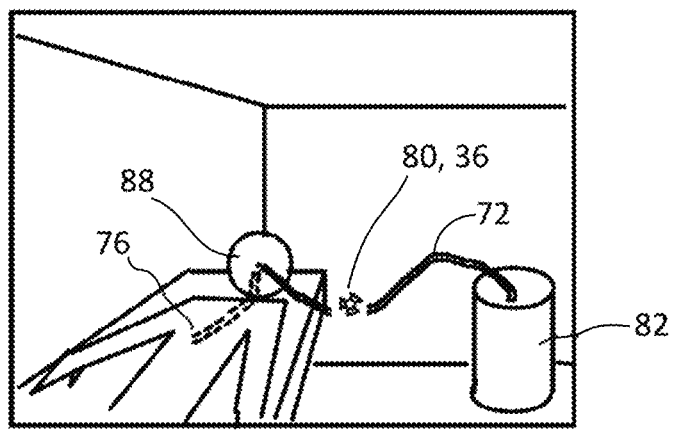
Figure 7C:
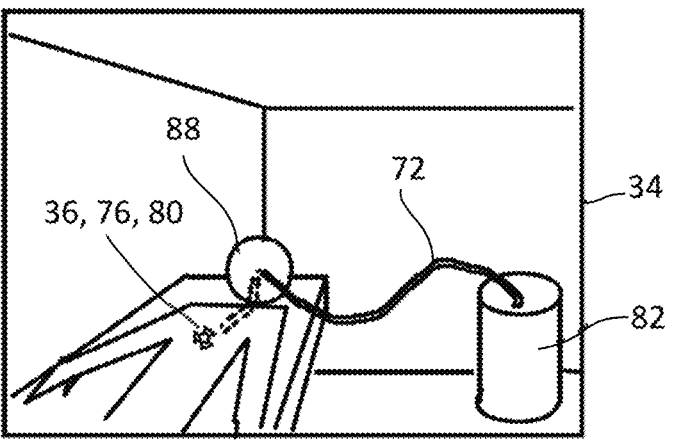

FIGS. 7A to 7C illustrate the operation of a system according to an embodiment of this presentation. FIG. 7A illustrates an image 34 produced by the apparatus 22 (not shown) of a system 70 such as shown in FIG. 6, where the distal end 76 of catheter 72 has been introduced in an orifice of the body of a patient 88 close to a region of the body that is to be treated (e.g. a lung). In FIG. 7A, the radiation source 80 of system 70 is contained in shield enclosure 82 and it is therefore not visible to apparatus 22, which does therefore display no radiation source marker in image 34.

FIG. 7B illustrates the same patient 88 and system 70 as in FIG. 7A, where radiation source actuator 84 has been actuated so as to move radiation source 80 through catheter 72 toward distal end 76. FIG. 7B shows source 80 mid-way in the catheter between shield enclosure 82 and distal end 76. Because source 80 is not shielded by the catheter, it is visible to apparatus 22, which displays radiation source marker 36 in image 34, above the position of source 80 in catheter 72.

FIG. 7C illustrates the same patient 88 and system 70 as in FIGS. 7A and 7B, where radiation source actuator 84 has been actuated further so as to move radiation source 80 through catheter 72 up to its distal end 76, where apparatus 22 displays radiation source marker 36. According to embodiments of this presentation, system 70 can be arranged to measure the time source 80 is visible to apparatus 22, and eventually arranged to issue an alarm signal if said measured time goes beyond a predetermined time. According to an embodiment of this presentation, processor 86 can be arranged to determine the outline of patient 88 in image 34 (for example using the heat signature of the patient, if camera 14 is also sensitive to infrared, or using shape recognition routines), and arranged to issue an alarm signal if the radiation source remains more than a predetermined time outside the shield enclosure and outside of said outlines of patient 88. Such an alarm signal would for example automatically protect the patient from undue exposure to radiations in case the caregiver did not move source 80 far enough in catheter 72 (and for example located source 80 as shown in FIG. 7B instead of as shown in FIG. 7C as desired).

Further, because as illustrated in FIGS. 7A to 7C the system 70 allows a user to safely monitor in real time the position of source 80 outside of shield enclosure 82 using source marker 36, system 70 allows a user to immediately act if source 80 is not located where it should be located, or does not move as it should move when actuated, or if anything abnormal is detected. Consistently with the operation illustrated in FIGS. 5A to 5C, the apparatus 22 of system 70 can also allow localizing rapidly a source 80 that becomes accidentally detached from wire actuator 84.

Figure 8:
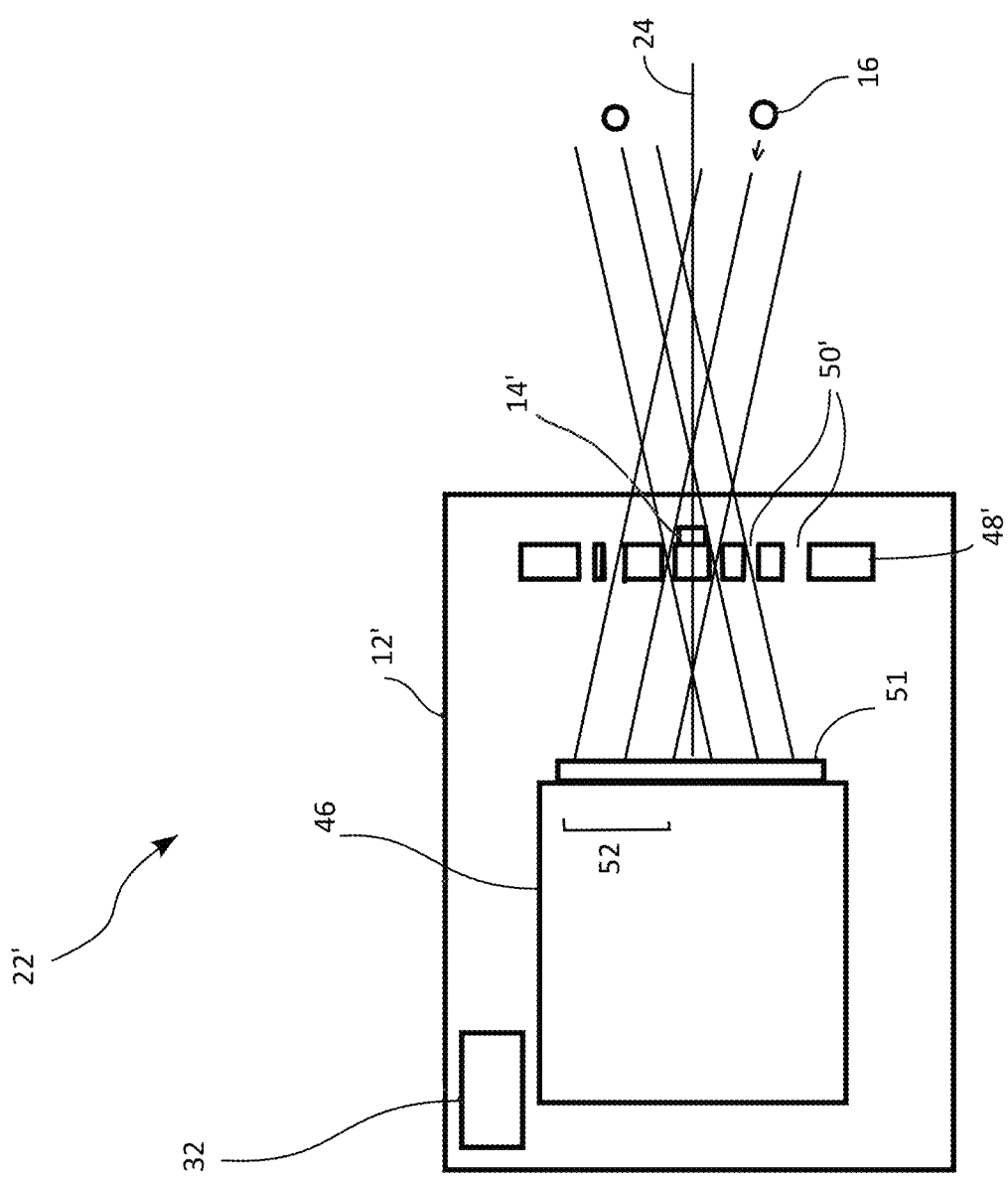
FIG. 8 illustrates an embodiment of an apparatus according to this presentation for visualizing a movable radiation source.

FIG. 8 illustrates an embodiment of a compact apparatus 22' for visualizing a movable radiation source 16 according to an embodiment of this presentation; the apparatus comprising a radiation angular position sensor 12' that can be essentially the same as the sensor illustrated in FIG. 4, but where the radiation mask 48' is such that it comprises no aperture along the axis 24 of the sensor. According to an embodiment of this presentation, the camera 14' is arranged in front of mask 48' and is aligned with axis 24; the camera 14' (comprising for example a semiconductor sensor and appropriate lenses) having a size such that it does not prevent radiations emitted by source 16 from passing through the coded aperture 50' of mask 48'. According to an embodiment, camera 14' can be sized so as to not overlap any opening 50' of mask 48'. Camera 14' can for example have a 6×6 $mm^2$ cross-section (or smaller, using for example a phone camera module) along a plane normal to axis 24. According to an embodiment, camera 14 has negligible absorption compared with mask 48'. The operation of apparatus 22' is similar to the operation of apparatus 22 as detailed above, and apparatus 22 and 22' can be both used to manufacture a system such as illustrated in FIG. 6.

Modifications, additions, or omissions may be made to the systems, apparatuses, and methods described herein without departing from the scope of the inventive concepts. The components of the systems and apparatuses may be integrated or separated. Moreover, the operations of the systems and apparatuses may be performed by more, fewer, or other components. The methods may include more, fewer, or other steps. Additionally, steps may be performed in any suitable order. As used in this document, "each" refers to each member of a set or each member of a subset of a set.

To aid the Patent Office, and any readers of any patent issued on this application in interpreting the claims appended hereto, applicants wish to note that they do not intend any of the appended claims or claim elements to invoke paragraph 6 of 35 U.S.C. Section 112 as it exists on the date of filing hereof unless the words "means for" or "step for" are explicitly used in the particular claim.

What is claimed is:

1. An apparatus for visualizing a movable radiation source, the apparatus comprising:
    a radiation angular position sensor arranged for generating an angular position, with respect to a sensor axis, of a radiation source emitting radiation in front of said radiation angular position sensor;
    a camera having a camera axis distinct from the sensor axis;
    a light diverter arranged in front of said radiation angular position sensor for diverting toward the camera, light originally emitted in front of said radiation angular position sensor toward the radiation angular position sensor, the light diverter being arranged to not change the direction of radiation emitted in front of said radiation angular position sensor; wherein the radiation angular position sensor has a first field of view and the camera has, together with the light diverter, a second field of view different from the first field of view; and
    a composite image generator arranged for:
    calculating a source position of the radiation source in a camera image captured by the radiation, said source position having errors due to the second field of view being different from said first field of view;
    generating a corrected position, derived from said angular position and automatically scaled to the camera image size and resolution, wherein said errors due to the second field of view being different from said first field of view are corrected; and
    adding a radiation source marker to said camera image captured by the camera at said corrected position.

2. The apparatus of claim 1, wherein said radiation angular position sensor comprises a pixelated radiation sensor having said radiation sensor axis, a radiation mask with a coded aperture being arranged in a plane normal to said radiation sensor axis in front of said pixelated radiation sensor.

3. The apparatus of claim 1, wherein said light diverter comprises a mirror arranged for reflecting light and letting radiation pass through.

4. The apparatus of claim 1, wherein the composite image generator is arranged to be calibrated by, in an initial state, moving a radiation source to at least two source positions in the field of view of the radiation sensor, recording at least two angular positions provided by the sensor at said at least two source positions and recording at least two corresponding camera positions of a picture of said radiation source in a camera image captured by the camera; calculating a sensor distance between said at least two source positions based on said at least two angular positions; calculating a camera distance between said at least two corresponding camera positions; and calculating a ratio of said sensor distance and said camera distance; the composite image generator being arranged to use said ratio for automatically scaling said position derived from said angular position to the camera image size and resolution.

5. The apparatus of claim 4, wherein said composite image generator comprises a user interface arranged for allowing a user to point to positions of a picture of the radiation source in said camera image, the composite image generator being arranged for storing said positions as well as corresponding angular positions generated by the sensor.

6. The apparatus of claim 1, wherein said light is comprised in the wavelength range of 300 nm to 1 mm.

7. The apparatus of claim 6, wherein said light is comprised in the wavelength range of 380 nm to 750 nm.

8. The apparatus of claim 1, wherein said radiation is comprised in the wavelength range of 0.01 to 10 nanometers.

9. The apparatus of claim 8, wherein said radiation is comprised in the wavelength range of 0.01 to 1 nanometers.

10. The apparatus of claim 8, wherein said radiation has energies comprised in the range of 100 eV to 1 MeV.

11. The apparatus of claim 1, wherein said radiation angular position sensor is arranged for generating said angular position for a radiation source having an intensity comprised between 1 microCuries and 100 Curies, located in a range of 0.5 to 100 meters from said sensor.

12. The apparatus of claim 1, wherein said radiation sensor, said camera and said composite image generator are arranged to generate a new composite image with a period comprised between 1 millisecond and 1 hour.

13. A brachytherapy system comprising:
    a catheter having a lumen between a distal end and a proximal end;
    a radiation source capable of passing through said lumen;
    a shield enclosure arranged for receiving the radiation source, the proximal end of the catheter being coupled to the shield enclosure;
    a radiation source actuator arranged for moving the radiation source out of the shield enclosure into said lumen toward the distal end of the catheter; and
    an apparatus as recited in claim 1, arranged for visualizing said radiation source in said catheter.

14. The brachytherapy system of claim 13, comprising a processor arranged to issue an alarm signal if the radiation source is outside the shield enclosure and does not move despite the radiation source actuator being actuated; or if the radiation source remains more than a predetermined time outside the shield enclosure and outside of outlines of a patient.

15. The brachytherapy system of claim 14, wherein the camera is arranged for detecting infrared light.

16. An apparatus for visualizing a movable radiation source, the apparatus comprising:
    a radiation angular position sensor comprising a pixelated radiation sensor having a radiation sensor axis, a radiation mask with a coded aperture being arranged in a plane normal to said radiation sensor axis in front of said pixelated radiation sensor; where said radiation mask comprises no aperture along said radiation sensor axis; the radiation angular position sensor being arranged for generating an angular position, with respect to said radiation sensor axis, of a radiation source emitting radiation in front of said radiation angular position sensor;
    a camera having a camera axis identical to the sensor axis; the camera being arranged in front of said radiation mask and being sized so as to not overlap an aperture of the mask; wherein the radiation angular position sensor has a first field of view and the camera has a second field of view different from the first field of view; and a composite image generator arranged for:

calculating a source position of the radiation source in a camera image captured by the radiation, said source position having errors due to the second field of view being different from said first field of view;

generating a corrected position, derived from said angular position and automatically scaled to the camera image size and resolution, wherein said errors due to the second field of view being different from said first field of view are corrected, and adding a radiation source marker to said camera image captured by the camera at said corrected position.

17. The apparatus of claim 16, wherein the composite image generator is arranged to be calibrated by, in an initial state, moving a radiation source to at least two source positions in the field of view of the radiation sensor, recording at least two angular positions provided by the sensor at said at least two source positions and recording at least two corresponding camera positions of a picture of said radiation source in a camera image captured by the camera; calculating a sensor distance between said at least two source positions based on said at least two angular positions; calculating a camera distance between said at least two corresponding camera positions; and calculating a ratio of said sensor distance and said camera distance; the composite image generator being arranged to use said ratio for automatically scaling said position derived from said angular position to the camera image size and resolution.

18. The apparatus of claim 17, wherein said composite image generator comprises a user interface arranged for allowing a user to point to positions of a picture of the radiation source in said camera image, the composite image generator being arranged for storing said positions as well as corresponding angular positions generated by the sensor.

19. The apparatus of claim 16, wherein said light is comprised in the wavelength range of 300 nm to 1 mm.

20. The apparatus of claim 19, wherein said light is comprised in the wavelength range of 380 nm to 750 nm.

21. The apparatus of claim 16, wherein said radiation is comprised in the wavelength range of 0.01 to 10 nanometers.

22. The apparatus of claim 21, wherein said radiation is comprised in the wavelength range of 0.01 to 1 nanometers.

23. The apparatus of claim 21, wherein said radiation has energies comprised in the range of 100 eV to 1 MeV.

24. The apparatus of claim 16, wherein said radiation angular position sensor arranged for generating said angular position for a radiation source having an intensity comprised between 1 and 12 Curies, located in a range of 0.5 to 10 meters from said sensor.

25. The apparatus of claim 16, wherein said radiation sensor, said camera and said composite image generator are arranged to generate a new composite image with a period comprised between 1 and 100 milliseconds.

26. A brachytherapy system comprising:

a catheter having a lumen between a distal end and a proximal end;

a radiation source capable of passing through said lumen;

a shield enclosure arranged for receiving the radiation source, the proximal end of the catheter being coupled to the shield enclosure;

a radiation source actuator arranged for moving the radiation source out of the shield enclosure into said lumen toward the distal end of the catheter; and an apparatus as recited in claim 16, arranged for visualizing said radiation source in said catheter.

27. The brachytherapy system of claim 26, comprising a processor arranged to issue an alarm signal if the radiation source is outside the shield enclosure and does not move despite the radiation source actuator being actuated.

28. The brachytherapy system of claim 26, comprising a processor arranged to determine the outline of a patient in the image acquired by the camera, and arranged to issue an alarm signal if the radiation source remains more than a predetermined time outside the shield enclosure and outside of said outlines of a patient.

29. The brachytherapy system of claim 28, wherein the camera is arranged for detecting infrared light.

* * * * *